United States Patent
Erdei et al.

(10) Patent No.: US 11,134,838 B2
(45) Date of Patent: Oct. 5, 2021

(54) METHOD AND SYSTEM FOR MEASURING VISUAL ACUITY

(71) Applicant: Medicontur Medical Engineering Ltd., Zsambek (HU)

(72) Inventors: Gabor Erdei, Budapest (HU); Csilla Fulep, Budapest (HU)

(73) Assignee: MEDICONTUR MEDICAL ENGINEERING LTD.

( * ) Notice: Subject to any disclaimer, the term of this patent is extended or adjusted under 35 U.S.C. 154(b) by 197 days.

(21) Appl. No.: 16/394,388

(22) Filed: Apr. 25, 2019

(65) Prior Publication Data

US 2019/0246893 A1 Aug. 15, 2019

Related U.S. Application Data

(63) Continuation-in-part of application No. 16/321,293, filed as application No. PCT/HU2016/000050 on Jul. 29, 2016, now abandoned.

(51) Int. Cl.
| | |
|---|---|
| A61B 3/032 | (2006.01) |
| A61B 3/00 | (2006.01) |
| G06F 17/15 | (2006.01) |
| G06F 17/17 | (2006.01) |

(52) U.S. Cl.
CPC ............ *A61B 3/032* (2013.01); *A61B 3/0033* (2013.01); *G06F 17/15* (2013.01); *G06F 17/17* (2013.01)

(58) Field of Classification Search
CPC .... A61B 3/00; A61B 3/02; A61B 3/10; A61B 3/14; A61B 3/032; A61B 3/0033; A61B 3/0025; A61B 3/0058; A61B 3/028; A61B 3/113; G06F 17/15; G06F 17/17
USPC ....... 351/205, 211, 222, 223, 239, 237, 243, 351/246
See application file for complete search history.

(56) References Cited

U.S. PATENT DOCUMENTS

2012/0229758 A1* 9/2012 Marin ............... G02C 7/02
351/159.52

FOREIGN PATENT DOCUMENTS

| CN | 101313843 | * 12/2008 | ............ A61B 3/032 |
| GB | 2355540 | * 4/2001 | ............ A61B 3/032 |

OTHER PUBLICATIONS

English translation of CN 101313842, Machine translated on Oct. 2, 2020.*

* cited by examiner

*Primary Examiner* — Jie Lei
(74) *Attorney, Agent, or Firm* — Olson & Cepuritis, Ltd.

(57) ABSTRACT

Visual acuity of a subject is ascertained by displaying to the subject sets of symbols having a different size, recording the subject's responses identifying each symbol, calculating a rate of recognition for each symbol size, and determining the client's visual activity based on the rate of recognition.

11 Claims, 7 Drawing Sheets

METHOD AND SYSTEM FOR MEASURING VISUAL ACUITY

CROSS-REFERENCE TO RELATED APPLICATIONS

This application is a continuation-in-part of U.S. patent application Ser. No. 16/321,293, filed on Jan. 28, 2019 as a 371 National Stage of International Patent Application No. PCT/HU2016/000050, filed on Jul. 29, 2016, each of which is incorporated herein by reference.

TECHNICAL FIELD

The invention relates in general to clinical visual acuity measurements. In particular, and not by way of limitation, the present invention is directed to a method, a system and a non-volatile storage medium containing a computer program for the measurement of visual acuity of a subject.

BACKGROUND

Visual acuity is the most important ophthalmological quantity that describes the perceived resolving power of the human eye. Its measurement is based on symbol recognition. The standardized symbols used for testing vision are called optotypes and can be specially shaped characters (including letters and numbers) or geometric symbols. However, recognition depends not only on the optical properties of the eye, but also on cognitive and motor abilities. Due to this complexity, visual acuity value is influenced by the mental state, fatigue and environmental factors. In clinical practice, conventional measurements are performed using visual acuity charts, or eye charts. The subject's task is to correctly recognize the optotypes, the size of which is decreasing from line to line. According to the "line assignment" evaluation method, the visual acuity value corresponds to the smallest line, where the majority of the symbols is recognized correctly (See 1. Duane T. (2006). Duane's Clinical Ophthalmology, Lippincott Williams & Wilkins, CD-ROM Edition. http://www.oculist.net/downaton502/prof/ebook/duanes/index.html, and 2. International Council of Ophthalmology, Visual Functions Committee (1988). Visual Acuity Measurement Standard, ICO 1984, Italian Journal of Ophthalmology, II/I 1988, pp 1/15.)

The decimal metric of visual acuity is denoted by V, and is defined as $$V = \frac{1}{\alpha_0}$$

where $\alpha_0$ is the threshold angle of view of the stroke width of the smallest visible symbol in minutes of arc.

The measurement results are strongly influenced by many environmental parameters, such as the optotype style/contrast/color, the number of optotypes in a line, the illumination of the chart and the room, the testing distance, etc. There is no international standard for the parameter settings, but there are various traditional setups. For example, the ETDRS (Early Treatment of Diabetic Retinopathy Study) chart shown in FIG. 1 is used in lots of clinical studies and is considered as the US standard (Duane, 2006; International Council of Ophthalmology (ICO), 1984). It has a special layout with 5 letters in each line, where the spacing between the letters and between the lines equals the letter size. It is implemented with the so-called Sloan characters which have been devised specifically for visual acuity measurements to achieve approximately the same legibility for all the characters. The other settings are roughly uniform in most countries, but in some cases are very different.

The size of letters in the current eye charts decreases from line to line by a constant ratio of $10^{1/10}$ which is approximately 1.26. The choice of this constant ratio made it common to express visual acuity in terms of log MAR, i.e. the decimal-base logarithm of the Minimum Angle of Resolution:

$$Y = \log_{10}(\alpha_0)$$

which we denote by Y in order to clearly distinguish from V.

The accuracy of visual acuity measurements is affected by systematic and random (statistical) errors. The former is caused by the inappropriate adjustment of the measurement parameters and deteriorates the comparability of the results. The most important systematic error sources of visual acuity measurements using eye charts are changes of the viewing distance, the surrounding illumination of the room, and the background illumination of the test chart. Random errors occur in the scoring process due to delicate uncertainties of the subject's visual system and are intensified by the rough sampling of the letter size scale (e.g. 0.1 log MAR). For example, though the theoretical probability threshold is 50% (Duane, 2006; International Council of Ophthalmology (ICO), 1984), using the ETDRS charts (implemented with five letters per line) the actual threshold rises to 60%, 80%, or even 100% depending on the distribution of correctly recognized letters, which causes noticeable error in the results relative to theory. According to the literature, the random error of current line-assignment-based visual acuity measurements varies between 0.6 and 1.5 line ($\Delta V = 0.15 \ldots 0.41$ arcmin$^{-1}$ or $\Delta Y = 0.06 \ldots 0.15$ in log MAR units) for subjects with normal vision. This accuracy is sufficient for screening purposes as part of preventive health care, however, epidemiologic surveys and clinical research require higher precision and reliability as the successive measurements are to be compared to each other. Over and above, accurate and sensitive acuity measurements are especially important in clinical applications testing patients suffering from retinal diseases (e.g. age-related macular degeneration or diabetic macular edema to determine the need for treatment or its efficacy), or cataract and refractive surgery candidates with high visual expectations (to indicate the need for corneal or lens surgery, and to evaluate its outcome). For this purpose there exist several scoring methods based on recording answers for individual letters, instead of complete lines ("single-letter-scoring"). The special design of the ETDRS chart allows the examiner to recompense the subject's visual acuity by −0.02 log MAR unit for each correctly recognized letter, since there are traditionally 5 letters in a line (0.02=0.1/5). (See 1. Kaiser, P. K. (2009). Prospective Evaluation of Visual Acuity Assessment: a Comparison of Snellen Versus ETDRS Charts in Clinical Practice (an AOS Thesis), Transactions of the American Ophthalmological Society, 107:311-324; 2. Vanden Bosch, M. E., Wall, M. (1997). Visual acuity scored by the letter-by-letter or probit methods has lower retest variability than line assignment method, Eye, 11, 411-417; and 3. Hazel, C. A., Elliott, D. B. (2002). The dependency of log MAR visual acuity measurements on chart design and scoring rule. Optometry and Vision Science, 79(12), 788-792.) Correspondingly, the visual acuity value can be determined from the $T_c$ total number of correct identifications in the chart as:

$$Y = 1.1 - 0.02 \cdot T_c$$

Though this certainly refines the recorded score, its outcome does not correspond exactly to the theoretical 50% probability threshold. It is offset by approximately half a line (i.e. +0.05 log MAR) systematic error (Vanden Bosch, 1997; Hazel, 2002).

Both in conventional line assignment evaluation and single-letter-scoring the examiner registers whether the subject recognized the displayed letters correctly or not. This way the mere fact of recognition, or more precisely the recognition probability (P) is tested, whereby the answers are represented in binary digits, by zeros and ones, corresponding to incorrect/correct answers. The number of correctly identified letters divided by the total number of letters at a given letter size are called the "recognition probability" (P) at that letter size.

The inventors have realized that a substantial random error is due to the binary representation of the answers, because the human perception of characters is more complex than the above described binary scheme: in case of an incorrect answer it is not sure if the subject does not see the specific letter at all. In other words, mixing up similar letters, such as "P" and "F", implies a better vision, than misidentifying totally different ones, such as "B" and "A". Current visual acuity measurements do not take the similarity of the displayed and the identified letters into account.

Therefore it is an objective of the invention to increase the accuracy of visual acuity measurement by taking into account the similarities/differences between the applied optotypes in an objective way that is independent from the subject and the conditions of the measurement.

SUMMARY OF INVENTION

The present invention involves a method, a system and a storage medium containing a computer program, which solve the aforementioned problems, as well as other problems that will become apparent from an understanding of the following description.

Accordingly, the invention relates to a method for measuring visual acuity of a subject, said method comprising the steps of:
  providing a set of optotypes,
  providing a pre-calculated value of similarity for pairs of optotypes selected from the set of optotypes,
  displaying to the subject sub-sets of optotypes of the set of optotypes in different optotype size,
  receiving for each displayed optotype of one of said sub-set of optotypes of a given optotype size a response of the subject indicative of an optotype (identified optotype) selected from the set of optotypes,
  registering for each response a value of similarity corresponding to the pre-calculated value of similarity of the pair of optotypes consisting of the displayed optotype and the identified optotype indicated in the response,
  calculating a value of rate of recognition for each optotype size, the value of rate of recognition for a given optotype size being an average of the registered values of similarity for the responses to the optotypes displayed in the given optotype size,
  determining the visual acuity from the values of rate of recognition.

The invention further relates to a system for determining visual acuity of a subject, comprising a display device, an input device and a computing device having at least one processor and a storage medium containing a computer program comprising instructions which, when executed by at least one processor of a computing device, it is capable of causing the system to carry out the method according to the invention.

The invention further relates to a non-volatile storage medium containing a computer program comprising instructions which, when executed by at least one processor of a computing device, it is capable of causing the computing device to carry out the method according to the invention.

Further advantageous embodiments of the invention are defined in the attached dependent claims.

The most important advantage of the invention is that it increases the accuracy of visual acuity measurements and thereby decreases the uncertainty.

BRIEF DESCRIPTION OF DRAWINGS

Further details of the invention will be apparent from the accompanying figures and exemplary embodiments.

FIG. 2b shows the maximum correlation position of the two letters according to FIG. 2a.

DETAILED DESCRIPTION OF EMBODIMENTS

According to the present invention similarities/differences between the optotypes used for measuring visual acuity are taken into account. For this purpose similarities/differences between the optotypes are quantified on the mathematical basis of correlation calculation. A value of similarity is calculated for any two optotypes (a pair of optotypes) involved in the visual acuity measurement as a correlation value calculated for the given pair of optotypes. This metric is called "optotype correlation" (OC).

OC does not depend on how the subject exactly sees the optotypes; instead it compares optotypes in their original form in order to avoid subject-specific artifacts. In addition, the OC value cannot be affected by the optotype size either, only the shape of the optotype can be considered in its definition.

According to a preferred embodiment, calculation of the OC is carried out on the non-distorted, high-resolution black-and-white images of a set of optotypes to be used, where the images are represented as two-dimensional matrices.

The mathematical function that has been developed specifically for image comparison is called Pearson's correlation function, which characterizes similarity of two pictures according to:

$$\rho(p, q) = \frac{\sum_{x,y} [f(x, y) - \bar{f}] \cdot [g(x - p, y - q) - \bar{g}]}{\sqrt{\sum_{x,y} [f(x, y) - \bar{f}]^2 \cdot \sum_{x,y} [g(x - p, y - q) - \bar{g}]^2}}.$$

In the above equation f(x,y) and g(x,y) are the matrices of the two optotypes to be compared, p and q refer to the relative lateral shift between the matrices and $\bar{f}$ indicates the mean value of f(x,y) and $\bar{g}$ indicates the mean value of g(x,y). Pixel coordinates are denoted by x-y and p-q. The matrices of the optotypes are binary, square matrices, in which a character is covered by 150×150 elements (i.e. pixels). The cells of the black optotype are represented by 0s, while the cells of the white background are represented by 1s. Each optotype is surrounded by an additional 150 pixel-wide white border around the optotype in order to avoid numerical artifacts during the calculations. Possible values of ρ(p,q) are between −1 and +1, where +1 indicates identical matrices, larger values belong to more related matrices, 0 to a random selection, and −1 means that the two matrices are the inverse of each other (i.e. where the first matrix has black pixels the second matrix has white pixels and where the first matrix has white pixels the second matrix has black pixels). The value of ρ(p,q) significantly depends on how the two matrices are shifted relative to each other. For quantifying optotype correlation the two matrices are shifted to a position in which the Pearson's correlation function ρ(p,q) is at its maximum:

$$\rho = \max_{p,q} \{\rho(p,q)\}$$

which is hereinafter referred to as the Pearson's correlation value or simply Pearson's correlation.

Figure 2A:
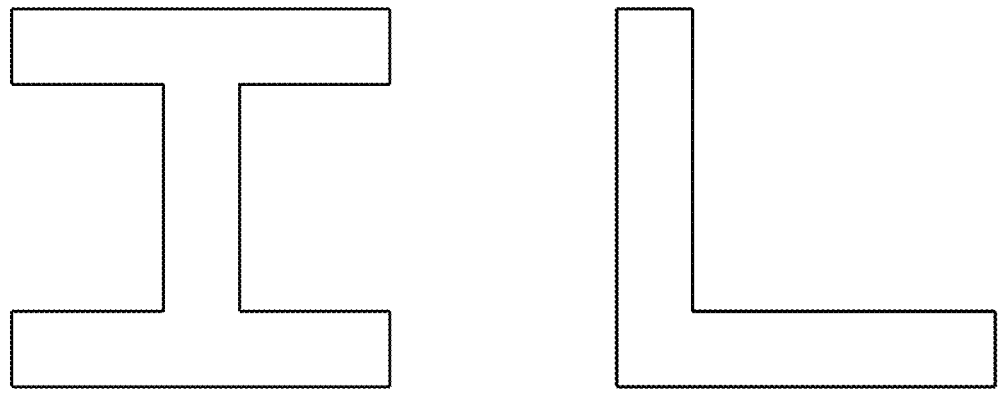
FIG. 2a shows the letters "L" and "I" in Sloan font type used in measuring visual acuity.
Figure 2B:
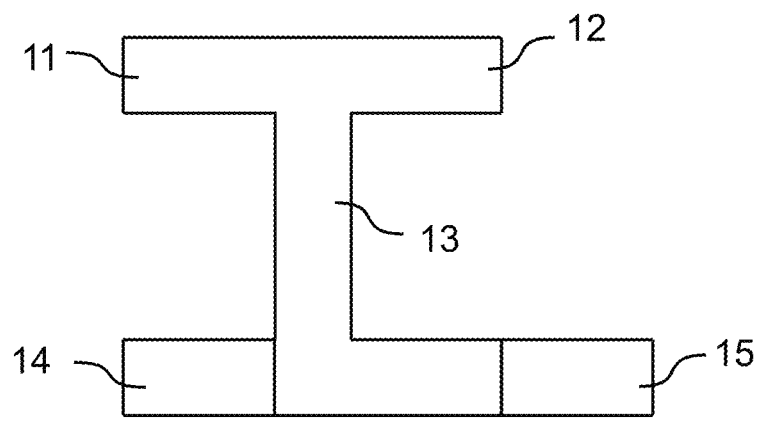

For an example see FIG. 2a showing the letters "L" and "I" in Sloan font type and FIG. 2b, where the two letters "I" and "L" are in maximum correlation position. In FIG. 2b areas 11, 12, 13, 14 belong to letter "I" and areas 13, 15 belong to letter "L" therefore area 13 corresponds to the area of overlap in the maximum correlation position.

According to a preferred embodiment the set of optotypes used consists of the extended Sloan font type, which contains all 26 letters of the English alphabet: the original Sloan letters (C, D, H, K, N, O, R, S, V, Z) complemented by additional Sloan-like letters of the English alphabet. The extended Sloan font type is a sansserif optotype set, where each character fills a square outline so that the stroke width is ⅕ of the letter size (see exemplary letters "I" and "L" in FIG. 2a).

The ideal OC distribution for random answers (i.e. comparing two randomly selected characters) in case of an ideal set of characters would have a large symmetric part with 0 expected value representing misidentifications and a small separate peak at 1 correlation, which refers to correct recognition. However, in reality, the letters of any alphabet are similar to each other to some extent, which is reflected in the fact that the expected value of ρ without the 1 correlations is higher than 0; in the case of the extended Sloan font type this expected value is 0.65. Thus the ρ Pearson's correlation values are not consistent with the usual true-false indications.

In order that the distribution of correlation values for random responses of the subject become consistent with the usual indication of false answers by zeros, the Pearson's correlation is transformed to obtain the new metric of OC:

$$OC = \frac{\rho - \bar{\rho}}{1 - \bar{\rho}},$$

where $\bar{\rho}$ indicates the expected value of the Pearson's correlation distribution without the unity values. The above linear transform ensures that the expected value of two randomly selected letters (i.e. misidentifications) equals 0 (the expected value of the numerator is zero, excluding identical letter pairs, i.e. accidental correct answers), and the correct recognitions are represented as unity (the denominator ensures that ρ=1 provides OC=1). In this way OC is directly comparable to the conventional binary scheme of true/false identifications. As an example the calculated values of OC for the first five letters of the English alphabet, rounded to two decimal places, in case of Sloan optotypes, are shown in Table 1, below.

TABLE 1

|   | A     | B     | C     | D     | E     |
|---|-------|-------|-------|-------|-------|
| A | 1     | −0.21 | −0.48 | −0.53 | −0.22 |
| B | −0.21 | 1     | 0.26  | 0.71  | 0.79  |
| C | −0.48 | 0.26  | 1     | 0.46  | 0.04  |
| D | −0.53 | 0.71  | 0.46  | 1     | 0.52  |
| E | −0.22 | 0.79  | 0.04  | 0.52  | 1     |

For identical letters the values are unity as can be seen in the main diagonal of the matrix. The entries of the OC matrix are symmetric with respect to the main diagonal of the matrix, which means that the OC value is independent of the role of the two letters being compared, e.g. the similarity, expressed by the OC value, is the same whether it is the letter "A" which is displayed and the letter "B" which is identified by the subject or if it is the letter "B" which is displayed and the letter "A" which is identified by the subject. Moreover, for more similar letters such as "B" and "E", the optotype correlation is larger (0.79) than for less similar letters such as "A" and "B" (−0.21).

Figure 3:
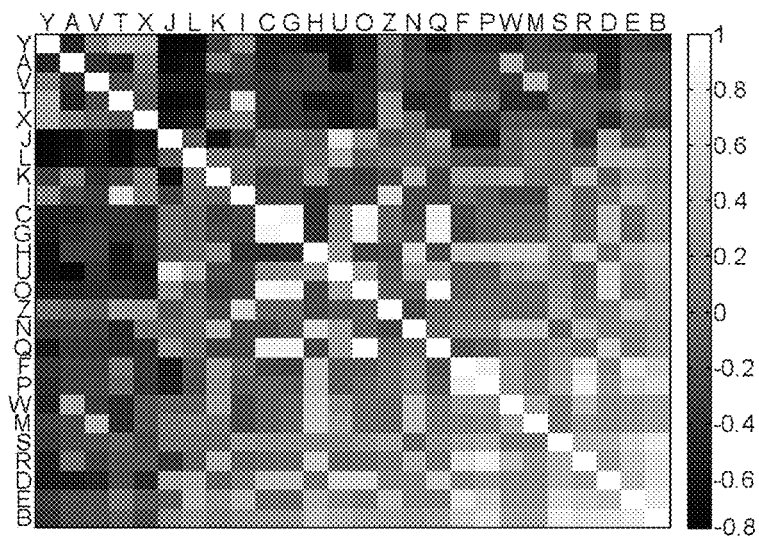
FIG. 3 is a greyscale-coded diagram illustrating the optotype correlation values for all 26 letters of the English alphabet (extended Sloan font).

The OC values for all 26 letters of the English alphabet (extended Sloan font) are illustrated in the greyscale-coded diagram of FIG. 3 where lighter shades correspond to higher similarity (white corresponding to OC=1) and darker shades corresponding to a lower degree of similarity.

It is also common to use charts which contain fewer letters than the English alphabet, such as the ETDRS Chart, which contains only the ten original Sloan letters, however, all letters of the complete English alphabet must be considered as potential guesses, because the subjects are not supposed to know this restriction. Due to this difference the numerical values of the OC matrix are slightly different for the ETDRS Chart as shown in Table 2, below, due to the linear transform of the Pearson's correlation which ensures that the expected value of misidentifications still equals 0.

TABLE 2

|   | C | D | H | K | N | O | R | S | V | Z |
|---|---|---|---|---|---|---|---|---|---|---|
| A | −0.539 | −0.592 | −0.380 | −0.033 | −0.343 | −0.558 | −0.057 | −0.255 | −0.429 | −0.150 |
| B | 0.227 | 0.695 | 0.468 | 0.117 | 0.253 | 0.320 | 0.685 | 0.798 | −0.226 | 0.322 |
| C | 1.000 | 0.435 | −0.467 | −0.344 | −0.251 | 0.861 | −0.046 | 0.152 | −0.456 | −0.076 |
| D | 0.435 | 1.000 | 0.091 | −0.079 | 0.172 | 0.567 | 0.351 | 0.448 | −0.523 | 0.171 |
| E | −0.005 | 0.497 | 0.388 | 0.214 | 0.166 | 0.125 | 0.565 | 0.629 | −0.228 | 0.430 |
| F | −0.290 | 0.218 | 0.461 | 0.212 | 0.148 | −0.146 | 0.662 | 0.333 | −0.351 | 0.011 |
| G | 0.883 | 0.441 | −0.433 | −0.264 | −0.142 | 0.827 | −0.013 | 0.165 | −0.385 | −0.096 |
| H | −0.467 | 0.091 | 1.000 | 0.124 | 0.583 | −0.299 | 0.522 | 0.172 | −0.382 | −0.253 |
| I | −0.276 | 0.090 | −0.438 | −0.076 | −0.252 | −0.298 | −0.081 | 0.167 | −0.369 | 0.583 |
| J | −0.045 | 0.271 | −0.122 | −0.709 | −0.067 | 0.162 | −0.023 | −0.023 | −0.601 | −0.181 |
| K | −0.344 | −0.079 | 0.124 | 1.000 | 0.320 | −0.371 | 0.343 | −0.068 | −0.449 | −0.218 |
| L | −0.115 | 0.343 | −0.029 | 0.035 | −0.018 | −0.123 | −0.117 | −0.012 | −0.641 | −0.019 |
| M | −0.138 | 0.193 | 0.537 | 0.009 | 0.437 | −0.017 | 0.257 | 0.119 | 0.388 | −0.063 |
| N | −0.251 | 0.172 | 0.583 | 0.320 | 1.000 | −0.110 | 0.367 | −0.019 | −0.379 | −0.264 |
| O | 0.861 | 0.567 | −0.299 | −0.371 | −0.110 | 1.000 | 0.014 | 0.209 | −0.485 | −0.108 |
| P | −0.147 | 0.296 | 0.463 | 0.163 | 0.152 | −0.078 | 0.824 | 0.369 | −0.318 | 0.016 |
| Q | 0.789 | 0.534 | −0.242 | −0.274 | −0.005 | 0.913 | 0.081 | 0.219 | −0.445 | −0.069 |
| R | −0.046 | 0.351 | 0.522 | 0.343 | 0.367 | 0.014 | 1.000 | 0.433 | −0.333 | 0.081 |
| S | 0.152 | 0.448 | 0.172 | −0.068 | −0.019 | 0.209 | 0.433 | 1.000 | −0.219 | 0.287 |
| T | −0.439 | −0.266 | −0.671 | −0.301 | −0.512 | −0.474 | −0.228 | −0.131 | −0.268 | 0.167 |
| U | 0.146 | 0.572 | 0.267 | −0.244 | 0.282 | 0.316 | −0.038 | 0.140 | −0.463 | −0.172 |
| V | −0.456 | −0.523 | −0.382 | −0.449 | −0.379 | −0.485 | −0.333 | −0.219 | 1.000 | −0.162 |
| W | −0.141 | 0.194 | 0.537 | 0.261 | 0.436 | −0.018 | 0.458 | 0.113 | −0.365 | −0.064 |
| X | −0.498 | −0.495 | −0.502 | 0.045 | −0.053 | −0.531 | −0.241 | −0.284 | −0.100 | 0.167 |
| Y | −0.583 | −0.613 | −0.708 | −0.347 | −0.394 | −0.612 | −0.548 | −0.389 | 0.049 | −0.079 |
| Z | −0.076 | 0.171 | −0.253 | −0.218 | −0.264 | −0.108 | 0.081 | 0.287 | −0.162 | 1.000 |

Figure 4:
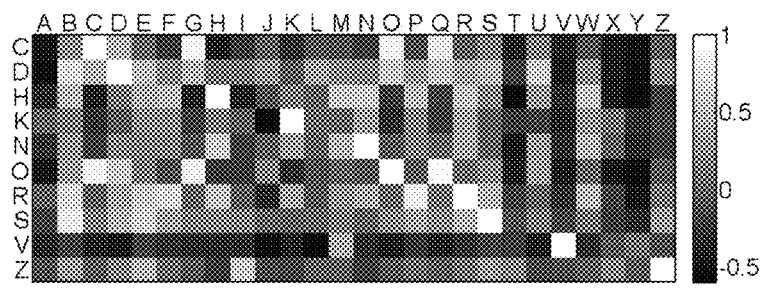
FIG. 4 is a greyscale-coded diagram illustrating the optotype correlation values between the 10 original Sloan characters (C, D, H, K, N, O, R, S, V, and Z) of the ETDRS Chart and all 26 letters of the English alphabet (extended Sloan font).

The OC matrix of the potential displayed-identified letter pairs for the ETDRS Chart is illustrated in the greyscale diagram of FIG. 4, where rows represent the displayed Sloan characters, columns indicate the potential identifications, and the OC values are greyscale-coded, where lighter shades correspond to higher similarity and darker shades corresponding to a lower degree of similarity.

As can be seen the OC matrix of the ETDRS Chart is not symmetric, however, the value of correct identifications (same displayed letter and identified letter) is still "1", the expected value of the misidentifications is 0 and the OC value is independent of the role of the two letters being compared (i.e. which is the displayed letter and which is the identified letter).

The OC matrix can be calculated for any set of optotypes of which all or only some may be used during the examination of a subject. The complete set of optotypes consists of all the possible identifications by the subject. For example, in case the ETDRS Chart is used the complete set of optotypes consists of the letters of the English Alphabet. Another common visual acuity test uses the Tumbling E eye chart which has the same scale as the standard ETDRS Chart, but all characters on the chart are a capital letter "E," in different spatial orientations (rotated in increments of 90 degrees), hence in this case the complete set of optotypes consists of the letter E rotated by 0, 90, 180 or 270 degrees.

In order to quantify visual acuity at a given optotype size a new metric is introduced, which is called rate of recognition (RR):

$$RR = \overline{OC},$$

and which is the average of OC values for the optotypes displayed at a given optotype size and the optotypes identified by the subject. The rate of recognition at a given optotype size is directly comparable to the recognition probability (P) at the same optotype size (which is the number of correctly identified optotypes divided by the total number of optotypes displayed at a given optotype size), but provides more information about vision.

In case of small letters (when the subject does not see the letters at all) the limit (corresponding to infinite number of random letters displayed) of the recognition probability is $P=1/26 \approx 0.04$ if we use all the twenty six letters of the English alphabet during the examination. The limit value of the rate of recognition for small letters (when the subject does not see the letters at all) is the average value of the whole OC matrix, including the unity values in the main diagonal, which is 0.04. This is in good agreement with the theoretical expectation of the recognition probability (P=1/26).

In case of large letters, when the subject sees every detail of the characters, both the rate of recognition and the recognition probability is 1 (the former corresponding to the average of the entries in the main diagonal of the OC matrix).

In the intermediate region, when the subject sees some blur from the optotypes, the RR is always somewhat larger than recognition probability (P).

As an illustration, let us evaluate a hypothetic answer "O C I V Y" of a subject for the following line on a standard ETDRS chart: "O C Z N V". The RR value would be (considering the OC values presented in Table 2):

$$RR = \frac{1 + 1 + 0.583 - 0.379 + 0.049}{5} = 0.4506,$$

while the recognition probability would be:

$$P = \frac{1+1+0+0+0}{5} = 0.400.$$

The eventual step is to determine the subject's visual acuity. In order to achieve the highest precision without any bias the acuity threshold is localized by fitting a psychometric function to the RR data obtained by measurement.

Due to its frequent application and simple analytical form the regression process can be based on the Weibull function W(u), which is generally used to fit a curve for recognition probability-letter size measurement values expressed in log MAR. Its mathematical formula is:

$$W(u) = 1 - \exp\left(-\left(\frac{u}{a}\right)^b\right),$$

where u denotes the independent variable of the function. Parameter "a" scales the width of the curve at its 1/e value, while parameter "b" sets the slope at the same point and also controls the kurtosis of the curve. According to the experience of the inventors, the Weibull function can be appropriately fitted to measured ($\alpha$, P) points ($\alpha$ in log MAR units) by three independent parameters: a, b, plus an additional lateral shift.

An even more robust fit can be obtained by further reducing the number of parameters by transforming the letter size values from log MAR space to decimal space, in which case the 1−W(u) function can be fitted precisely on the measured points by the two parameters "a" and "b" (having the same interpretation as in case of the Weibull function). The expression becomes:

$$SG(u) \equiv 1 - W(u) = \exp\left(-\left(\frac{u}{a}\right)^b\right),$$

which is called a Super-Gaussian (SG) function, if b>2. Such curves are platykurtic, i.e. they are broader and flatter than the standard Gaussian function. The above equation has to be further transformed linearly so that its limits correspond to the theoretically expected RR values.

After the linear transformation the fitting curve, which is also a Super-Gaussian function, takes the following form in decimal space:

$$SG'(v) = {}^{25}\!/\!{}_{26} \cdot SG(v) + {}^{1}\!/\!{}_{26},$$

where the argument of the transformed function is the reciprocal letter size v (where $\alpha$ is the angle of view of the stroke width of the letter in minutes of arc):

$$v \equiv \frac{1}{\alpha}$$

and the constants have been set so that SG'(0)=1, and SG'(v→∞)=1/26, in consistence with the 26 letters as potential answers (identifications) in the tests.

Figure 5:
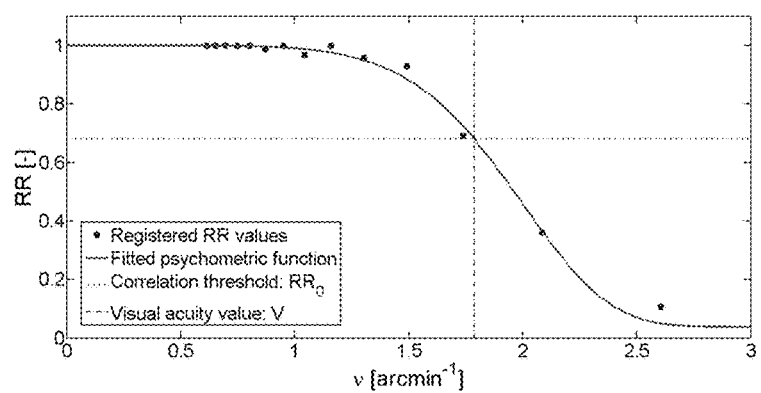
FIG. 5 is a graph showing typical rate of recognition (RR) results in decimal notations plotted against the reciprocal letter size measured in minutes of arc and the fitted psychometric function in the form of a Super-Gaussian function.

In FIG. 5, the RR results of a typical measurement are presented for a clear understanding of the relationship between RR obtained for a given optotype size and the reciprocal optotype size v, the term "optotype size" designates the angle of view of the stroke width of the optotype measured in minutes of arc. FIG. 5 presents the (v, RR) results of a typical measurement together with the fitted Super-Gaussian psychometric function.

Visual acuity (V) can be determined for a given subject from the Super-Gaussian curve fitted to their registered RR values. The measured acuity corresponds to the specific reciprocal letter size ($v_0$) at which the Super-Gaussian curve fitted on the RR values equals a given threshold ($RR_0$). This can be expressed mathematically as:

$$SG'(v_0)|_{a,b} = RR_0 \Rightarrow V \equiv v_0,$$

from which the visual acuity (V) value can be easily calculated, since $$\alpha_0 = \frac{1}{v_0}$$

and $$V = \frac{1}{\alpha_0}$$

Figure 6:
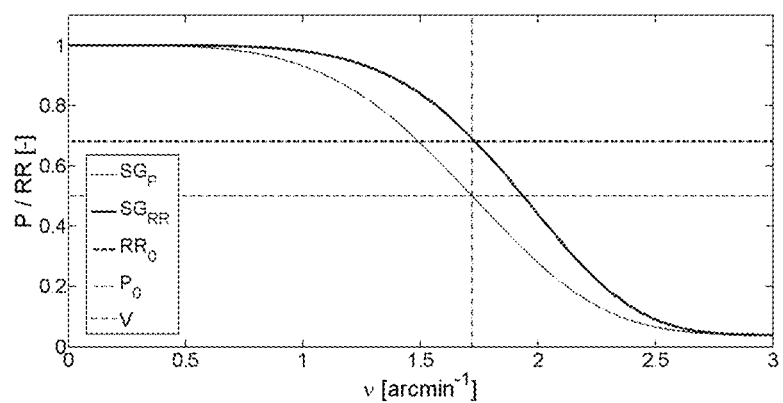
FIG. 6 is a graph showing average best-fit Super-Gaussian interpolation curves in probability and rate of recognition scoring with probability threshold and corresponding rate of recognition threshold for obtaining visual acuity.

The threshold rate of recognition $RR_0$ is preferably chosen so as to best correspond to the theoretical recognition probability threshold $P_0$=0.5 applied in measurements according to the ICO standard, whereby the method according to the present invention gives the same visual acuity results as the conventional ICO standard measurements, but with less random error. The inventors have analyzed visual acuity test results for a number of subjects and have determined and plotted both the recognition probability (P) values and the rate of recognition (RR) values against the reciprocal letter size v. The average best-fit Super-Gaussian interpolation curves in probability and rate of recognition scoring are shown in FIG. 6. As can be seen a threshold rate of recognition $RR_0$=0.68 provides the same threshold reciprocal letter size $v_0$ (and thereby the same visual acuity V) as what can be obtained from the theoretical recognition probability threshold $P_0$=0.5 value. The measurement results for ten subjects are summarized in Table 3. The pupil diameters, probability-scoring-based visual acuity values ($V_P$) at $P_0$=0.5 threshold, rate of recognition values calculated at $V_P$, and new visual acuity values ($V_{RR}$) at the determined rate of recognition threshold ($RR_0$=0.68) are shown in the columns of Table 3, below, for each subject. Visual acuity values are expressed in decimal units.

TABLE 3

| Subject | Pupil diameter [mm] | $V_P$ @ $P_0$ = 0.5 | RR @ $V_P$ | $V_{RR}$ @ $RR_0$ = 0.68 |
|---|---|---|---|---|
| Kl. Mi. | 6.0 | 1.27 | 0.63 | 1.25 |
| Ku. Ma. | 8.0 | 1.42 | 0.69 | 1.43 |
| R.I. | 5.0 | 1.46 | 0.75 | 1.50 |
| P.B. | 5.0 | 1.54 | 0.65 | 1.52 |
| M.T. | 5.6 | 1.63 | 0.72 | 1.67 |
| S.O. | 5.2 | 1.75 | 0.66 | 1.74 |
| G.T. | 6.2 | 1.77 | 0.73 | 1.82 |
| S.T. | 4.6 | 1.79 | 0.63 | 1.79 |
| G.A. | 5.0 | 1.87 | 0.73 | 1.90 |
| U.F. | 3.8 | 2.08 | 0.64 | 2.07 |

According to another preferred embodiment the more widespread log MAR units (i.e. s=$\log_{10}(\alpha)$) are used for the letter size expression. As discussed above, in case of decimal letter size expression the Super-Gaussian function provided an advantageous robust fit for the interpolation of the psychometric function, having only two independent parameters. However, switching the letter size expression from decimal to log MAR units, the regression function has to be changed as well. In this case, advantageously the L(s) sigmoid-shape logistic function can be applied, which is the most frequently used two-parameter curve to approximate any psychometric function on a log MAR scale. Its mathematical formula is described by:

$$L(s) = \frac{1}{1 + \exp(-k \cdot (s - s_{mp}))}. \quad (1)$$

The $s_{mp}$ parameter sets the midpoint position of the sigmoid, while k/4 determines the steepness of the curve at this point. To make sure that the limits of the psychometric function correspond to the theoretically expected RR values in case the set of optotypes consists of the letters of the English alphabet, it has to be further transformed linearly as:

$$L'(s) = \frac{25}{26} \cdot L(s) + \frac{1}{26}, \quad (2)$$

so that $\lim_{s \to \infty} L'(s)=1$ (large letters, when the subject sees every detail), and $\lim_{s \to -\infty} L'(s)=1/26$ (small letters, when the subject does not see the letters at all) as discussed above.

Visual acuity of a subject is determined by fitting the logistic curve L'(s) to their measured RR values collected at the discrete letter sizes of the eye chart (s=1.0, 0.9, 0.8, . . . , −0.3 log MAR). In accordance with the measurement standard, the Y visual acuity value corresponds to the specific $s_0$ letter size at which the value of the function equals the given threshold ($RR_0$):

$$L'(s)_{s=s_0}=RR_0 \Rightarrow Y \equiv s_0. \quad (3)$$

Figure 7:
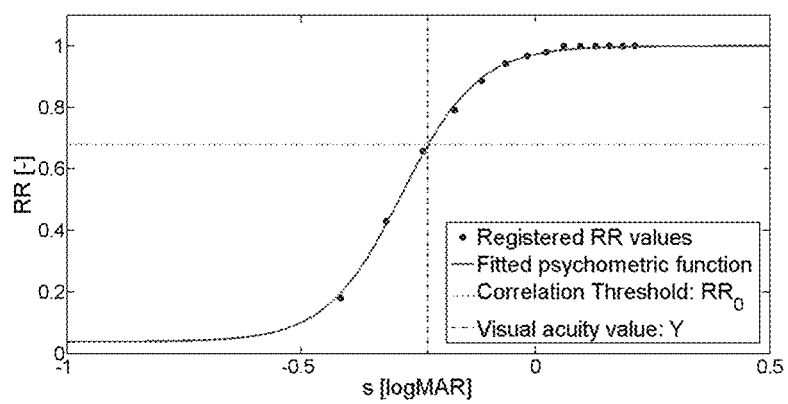
FIG. 7 is a graph showing typical rate of recognition (RR) results in log MAR notations and the fitted psychometric function in the form of a sigmoid-shape logistic function.

FIG. 7 shows the same visual acuity test results as FIG. 5 but in this case the measured Rate of Recognition (RR) values can be seen together with the fitted psychometric curve (L'(s)) as a function of the letter size s in log MAR notations.

Figure 8:
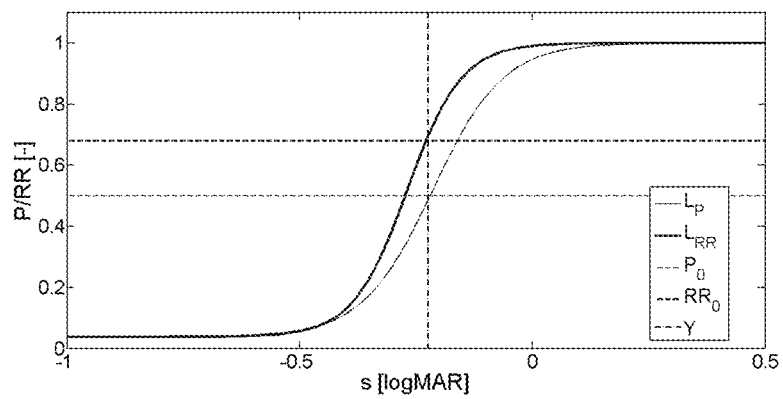
FIG. 8 is a graph showing average best-fit interpolation curves in probability and rate of recognition scoring shown in log MAR notations with probability threshold and corresponding rate of recognition threshold for obtaining visual acuity.

The correlation threshold can be calibrated empirically as explained above. Evaluating the same test results of a number of subjects using probability scoring and rate of recognition scoring the average best-fit interpolation curves in log MAR notations are shown in FIG. 8, $L_P'$ being the interpolation curve for probability scoring and $L_{RR}'$ being the interpolation curve for rate of recognition scoring. As before, the rate of recognition threshold $RR_0$=0.68 provides the same threshold letter size $s_0$ in log MAR (and thereby the same visual acuity Y) as what can be obtained from the theoretical recognition probability threshold $P_0$=0.5 value. In other words, the systematic error (between the visual acuity values obtained by correlation-based and traditional probability-scoring-based evaluation of the same trial records) reached its minimum at $RR_0$=0.68.

It is further noted that according to the examinations carried out, the difference between the visual acuity values obtained by the decimal and the log MAR notation is negligible.

The test results also demonstrated that the novel rate of recognition scoring according to the present invention significantly reduces the statistical error of visual acuity measurement. The statistical (random) error is affected by both the introduction of RR, and by increasing the number of optotypes used in the measurements. In order to separate these two effects, the test results were evaluated in four different ways. First, at each letter size of the standard ETDRS chart ($\Delta \log_{10}(\alpha)$=0.1 log MAR) 5 optotypes randomly selected from the original Sloan letters (C, D, H, K, N, O, R, S, V, Z) were examined by recognition probability. This corresponds to the conventional probability-scoring-based determination of visual acuity (test P5). Secondly, the same 5 letters at the same letter sizes were analyzed again, but based on the rate of recognition scoring in accordance with the present invention (test C5). Thirdly, all the 26 letters of the English alphabet were examined at each letter size of the densely sampled letter size scale ($\Delta \log_{10}(\alpha)$ 0.05 log MAR) by recognition probability (test P26). Finally, all the 26 letters were evaluated at each letter size of the densely sampled letter size scale with RR taken into account (test C26). One representative result for the outcome of these tests (P5, C5, P26, C26) is depicted in FIG. 9a in decimal notations and another representative result is depicted in FIG. 9b in log MAR notations.

Figure 9A:
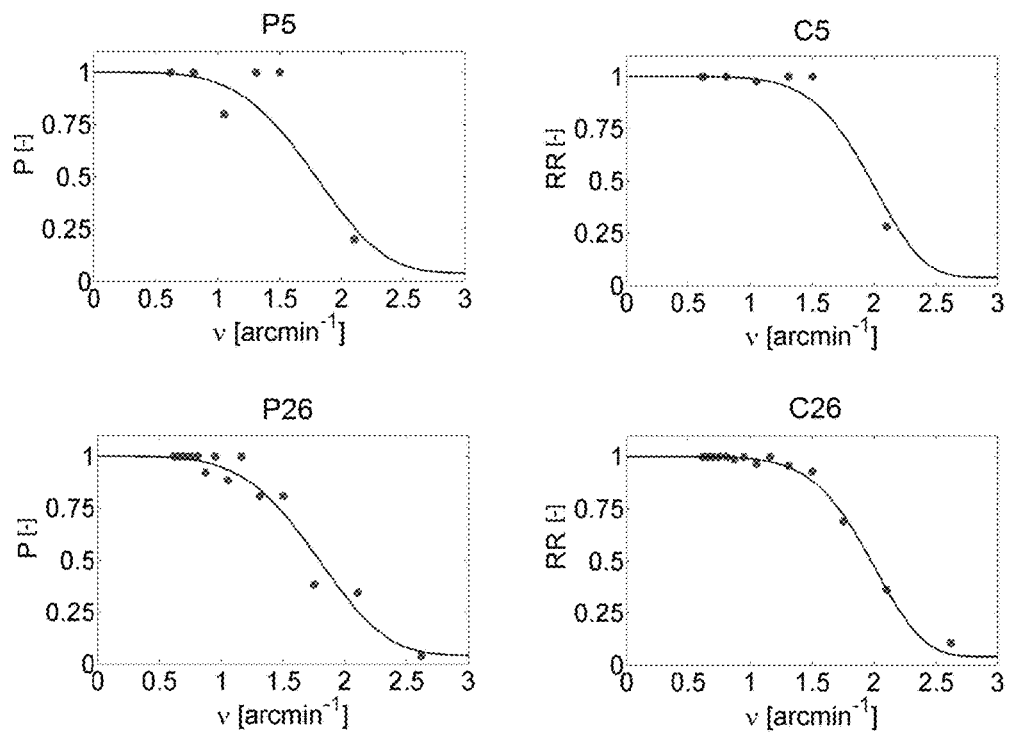
FIG. 9a shows four graphs in decimal notations containing representative results for the outcome of a visual acuity measurement evaluated in four different ways to illustrate the effect of the applied scoring method and the number of tested letters.
Figure 9B:
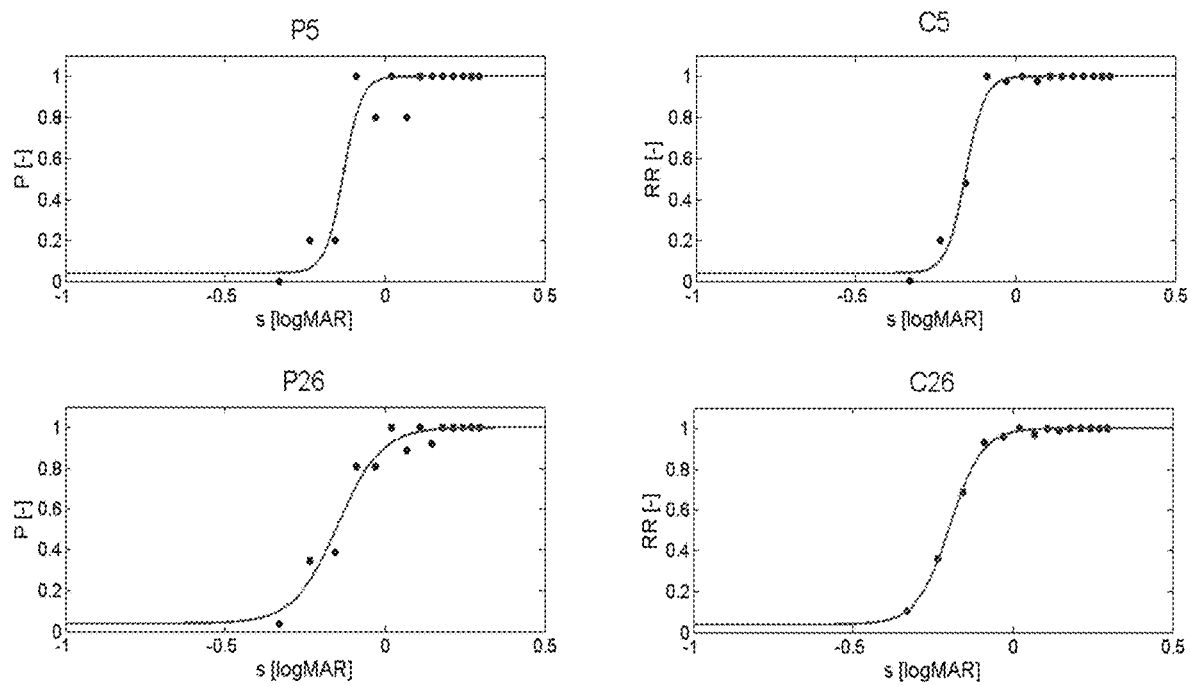
FIG. 9b shows four graphs in log MAR notations containing representative results for the outcome of the same visual acuity measurement carried out for a different subject as in case of FIG. 9a and evaluated in the same four ways to illustrate the effect of the applied scoring method and the number of tested letters.

In FIGS. 9a and 9b dots represent registered values, lines show the fitted psychometric function. "P" labels an evaluation process based on recognition probability, "C" refers to the inventive method using rate of recognition (correlation-based scoring). Evaluations marked with "5" were performed with only 5 examined characters selected from the ETDRS chart at each letter size of the sparsely-sampled standard letter size scale (0.1 log MAR), and "26" refers to evaluations made with all the 26 letters of the English alphabet at each letter size of the densely-sampled letter size scale 0.05 log MAR).

The test results indicated that both the larger database (26 letters) and the utilization of RR decreases the statistical error as expected. The former reduced the error to its $1/\sqrt{10}$ value, since tests P26 and C26 contained two times as many letter sizes and five times as many letters at each size than tests P5 and C5. According to the experiments, the correlation-based scoring decreases uncertainty by ~28% in case of special laboratory measurements testing all 26 letters of the English alphabet at 14 examined letter sizes ranging from 0.3 log MAR to −0.35 log MAR with ~0.05 log MAR increment.

Another examination showed that the application of correlation-based scoring in itself reduced the statistical error by ~20% in standard clinical environment (i.e. testing five-letter lines with 0.1 log MAR size increment). Based on the results, in this case, the uncertainty error decreased by 0.0083 log MAR thanks to RR. This significant improvement justifies the extra requirements of the correlation-based approach in the clinical practice as well.

In order to demonstrate the significance of the error reduction caused by the modification of the scoring method, the number of tested letters per size were determined that would be required for the probability-based evaluation to provide the same error as correlation-based scoring with five letters tested. The examination showed that the precision of probability-based evaluation in case of 10 tested letters per letter size approximately equals that of the RR-based evaluation in case of 5 letters per letter size. This observation shows that the utilization of the correlation-based scoring affects the results in the same way as the duplication of the number of tested letters, however, it does not increase the duration of the test proportionally.

The special laboratory measurements predicted 28% statistical error reduction when using the correlation-based method instead of probability-based scoring, while the clinical trials showed that under standard ophthalmological conditions the error reduction is 21% in case of 10 letters, and it is 19% with five letters per line. From this it can be concluded that the extent of the error reduction caused by replacing probability-based scoring with correlation-based approach depends on the measurement conditions, such as the number of tested characters, the applied letter sizes, the surrounding illumination of the room, the viewing distance, etc., however, the error reduction is always significant.

In the following, a system and a method according to the present invention will be described for performing visual acuity measurement by correlation-based scoring.

Figure 10:
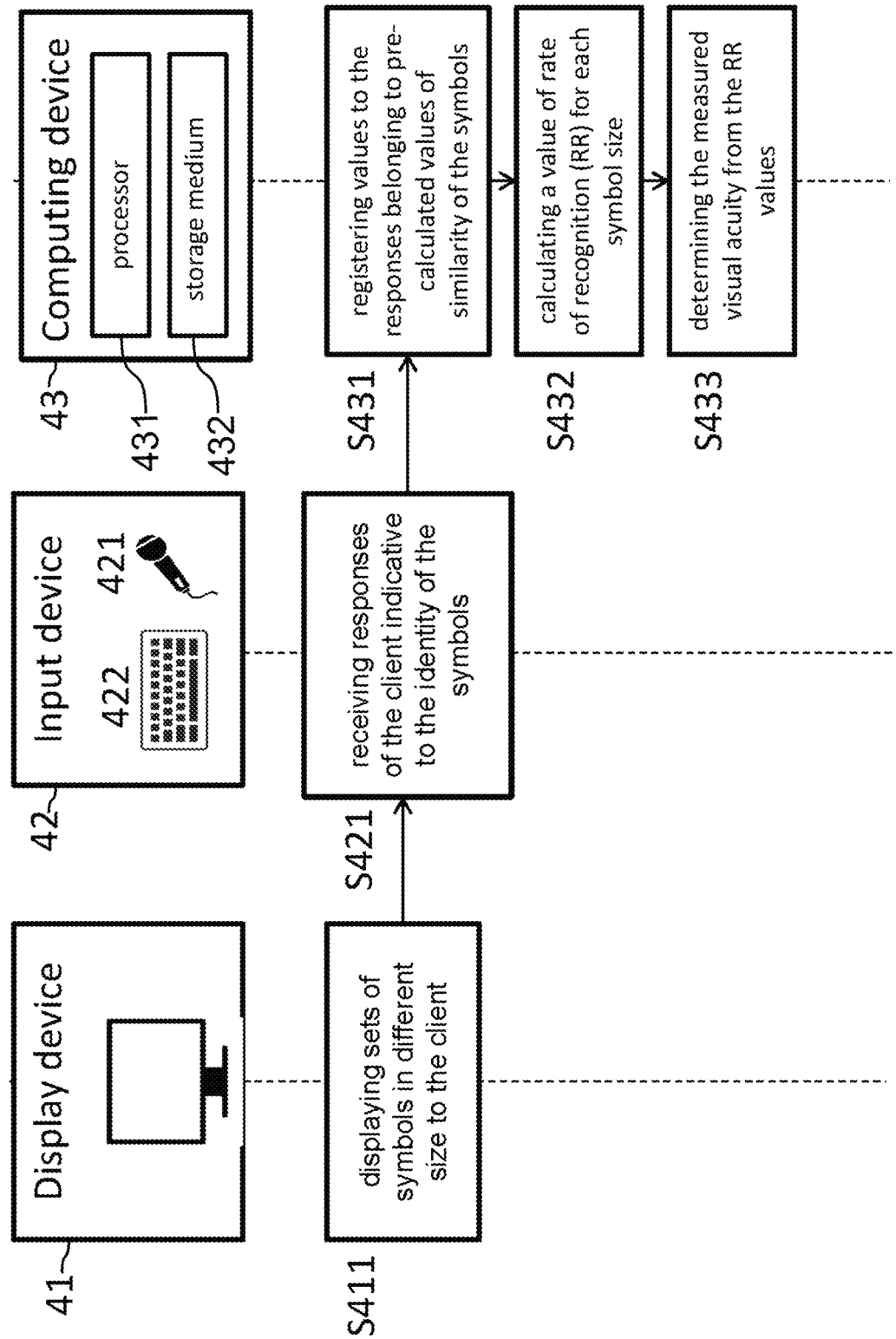
FIG. 10 is a combined block diagram of an exemplary system according to the invention and a flow chart of an exemplary method according to the invention.

In FIG. 10 a combined block diagram of an exemplary system according to the invention and a flow chart of an exemplary method according to the invention is illustrated for measuring visual acuity. The system comprises a display device 41, an input device 42 and a computing device 43.

A set of optotypes (also referred to as the "complete" set of optotypes) are provided, which consists of the potential identifications of displayed optotypes by a subject. For example, in case of using the ETDRS Chart the set of optotypes consists of the 26 letters of the English alphabet (extended Sloan font) even though only the 10 letters of the ETDRS Chart are actually used during the visual acuity measurement. Since the standard 10-letter ETDRS Chart is not known by the subject the potential identifications (answers) cover all 26 letters of the English alphabet.

Figure 1:
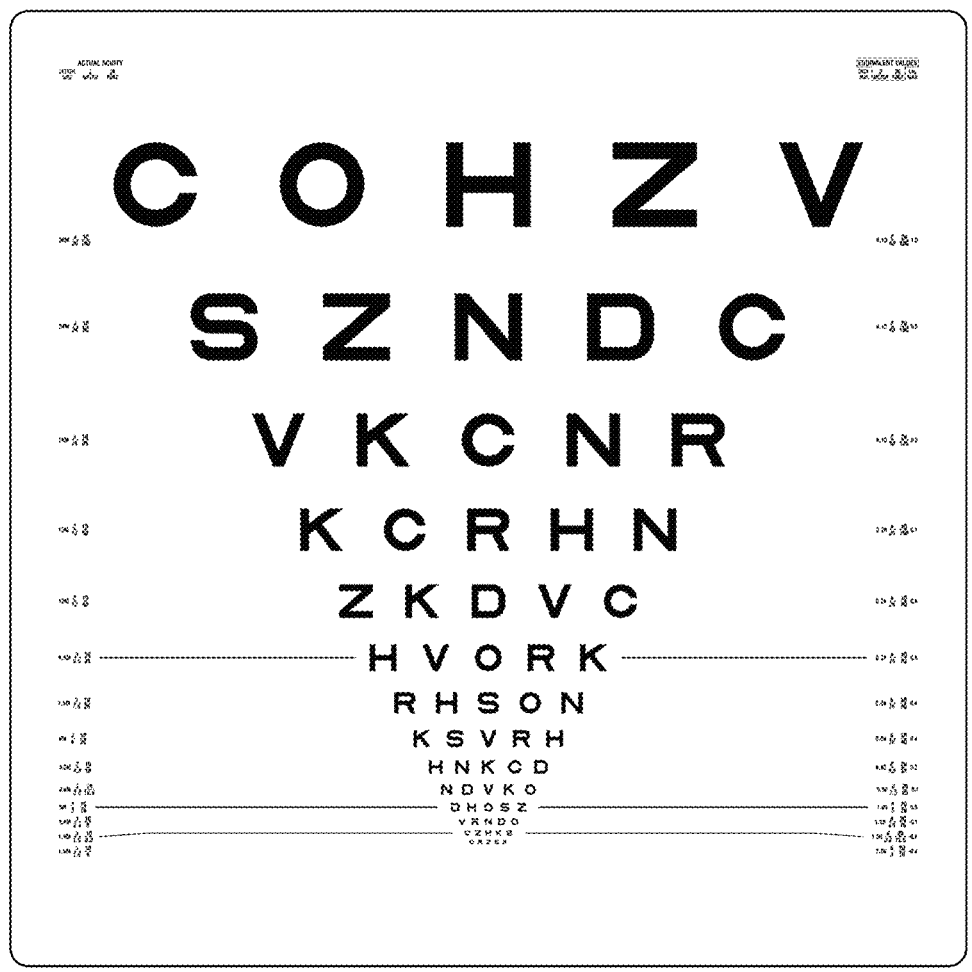
FIG. 1 is a standard prior art ETDRS visual acuity chart.

In Step S411 sub-sets of optotypes of the set of optotypes in different size are displayed to the subject on the display device 41. In the context of the present invention the sub-set of optotypes of the set of optotypes may include all or only some of the optotypes contained in the set of optotypes (the complete set). Furthermore, the sub-set of optotypes may contain more than one identical optotypes (e.g. the letter "C" may appear twice or more times within the sub-set of optotypes), in this sense, the sub-set may actually have more elements than the complete set, however, the sub-set is truly a sub-set in the sense that it cannot contain elements that are not comprised by the complete set as that would mean that optotypes unknown to the subject are being used, which the subject would not be able to identify even in case of perfect vision. The optotypes of each sub-set may be displayed separately (one by one) or simultaneously e.g. as in the standard ETDRS visual acuity chart illustrated in FIG. 1. Displaying the optotypes in sub-sets makes it possible to examine all optotypes of the complete set subsequently. Moreover, the special "one at a time" displaying method has for advantage that crowding has no influence on the measurement. Furthermore, the "one at a time" displaying method makes it possible to examine all optotypes of the complete set, e.g., all the twenty six capital letters of the English alphabet in each letter size, instead of the five characters printed in a line on the standard ETDRS visual acuity chart according to the prior art.

In Step S421 the input device 42 receives responses of the subject indicative of an identified optotype selected from the complete set of optotypes. The identified optotype may or may not correspond to the actually displayed optotype. Since the complete set of optotypes contains all the optotypes which the subject believes to be potentially displayed to him or her, the subject will select an optotype from this complete set regardless of the number of optotypes actually used in the test. For example if the standard ETDRS visual acuity chart is used containing only 10 letters of the English alphabet, the subjects responses may nevertheless relate to any letter of the English alphabet since a misidentification is not limited to the 10 letters actually used.

The responses may be voice or tactile reactions about the identity of the optotypes entered in the input device 42, depending on the type of input device 42 used. For example the input device 42 may comprise a microphone 421 for receiving an oral answer of the subject and a voice recognition module can be used to interpret the oral answer. The input device 42 may comprise a tactile reaction recognition module, such as a keyboard 422 for receiving a tactile reaction, e.g. pressing the letter on the keyboard 422 corresponding to the identified letter. The input device 42 is operative to receive responses of the subject indicative of the identity of the displayed optotypes. The received response is transmitted to the computing device 43 which transmission may be an internal data transmission within a computer.

The distinction between the display device 41, the input device 42 and the computing device 43 is based on the function carried out by these devices and not on the physical form in which the devices are implemented. For example, the display device 41, the input device 42 and the computing device 43 can be implemented in a single notebook having a keyboard and a monitor both forming an integral part of the notebook being the computing device itself which comprises a processor and memory capable of controlling the monitor for generating the images of the optotypes. In another embodiment the display device 41 can be a screen on a wall for displaying the images of the optotypes projected by a projector. The projector may be under the control of the notebook or it may be operated separately.

In step S431 the computing device 43 registers a value of similarity for each response. The value of similarity corresponds to a pre-calculated value of similarity of a pair of optotypes consisting of the displayed optotype and the identified optotype indicated in the response. In this step, a value of "1" is registered if the response of the subject is accurate, i.e. the optotype displayed on the display device 41 is identical to the optotype identified in the response. On the other hand, when the response of the subject is false, the pre-calculated value corresponding to the misidentification is registered. The pre-calculated value of similarity is a correlation value calculated for the given pair of optotypes. According to a preferred embodiment the correlation value is obtained as the optotype correlation (OC) calculated from the Pearson's correlation values as explained above. For example, using the 10 letters of the ETDRS Chart and using the above defined optotype correlation for quantifying the similarity between a displayed letter (selected from the 10 letters of the ETDRS Chart) and the subject's response (selected from the 26 letters of the English alphabet) the pre-calculated values of similarity correspond to the entries given in Table 2. Thus, in Step S431 the computing device 43 registers the entry of a specific row and column for which the column heading corresponds to the displayed letter and the row heading corresponds to the letter indicated in the response received in Step S421. For example, if the displayed optotype was "C" and the subject's response was "C", the registered value of similarity is "1". If the displayed optotype was "C", but the subject's response was "D", then the registered value is "0.435", which is the entry in the field of column "C" and row "D", see Table 2. Other than correlation functions can be introduced as well for quantifying the similarity between two optotypes selected from the complete set, for example mutual information (MI) or structural similarity (SSIM) can be used to calculate values of similarity between optotypes as will be apparent for a person skilled in the art.

In Step S432 the rate of recognition (RR) value is calculated for each optotype size. RR may be calculated as the average of the registered values of similarity for each optotype size. It is possible to calculate the rate of recognition for a given optotype size once the values of similarity are registered for all the optotypes displayed in the given size, or it is possible to wait until the values of similarity are registered for every optotype size and the RR values can be calculated for every optotype size.

In Step S433, the measured visual acuity is determined from the RR values. Determination preferably includes a step of fitting a function to the RR values of each optotype size. The RR values are plotted against a quantity related to the optotype size, such as optotype size in log MAR notations or reciprocal optotype size in decimal notations as explained above. The visual acuity is calculated from the optotype size belonging to a rate of recognition threshold ($RR_0$). The threshold $RR_0$ is preferably calibrated based on previous measurements or the above described methods and threshold are used in order to ensure that the result of the measurement is consistent with conventional visual acuity measurements.

According to a preferred embodiment the computing device 43 comprises at least a processor 431 and a storage medium 432 containing a computer program comprising instructions which, when executed by the least one processor 431 of the computing device 43 is capable of causing the computing device 43 to carry out the Steps S431, S432, S433.

Example

In an exemplary measurement setup the set of optotypes consisted of the letters of the English alphabet. The optotypes were presented to the subject one by one on a computer screen (LCD monitor) serving as the display device 41. The test distance has been selected to be large enough to ensure accommodation-free measurements. The depth of field of the human eye is ¼ diopter, which means that the test distance is preferably at least 4 meters. An in-plane-switching LCD monitor was used, with a pixel pitch of 0.265 millimeter in order to display the optotypes with large resolution, the test distance was set to 9.5 meters. This relatively large distance allowed for a denser sampling of the visual acuity scale ($\Delta$ log MAR$\approx$0.05) than attainable in clinical measurements, which further decreases the error of the results. For the measurement a total of 14 optotype sizes were used for which the stroke width of the optotypes was an integral multiple of the pixel pitch. Since the human pupil is wider under mesoscopic than photopic conditions, the measurements were carried out in a darkened room, with an illuminance of around 10 lux (i.e. 3.2 cd/m$^2$ average luminance). In such an environment the refractive errors (chromatic and higher order monochromatic aberrations) have more significant effect on visual acuity. The luminance of the monitor was 90 cd/m$^2$-s that fulfills the ICO standard (min. 80 cd/m$^2$). The above described measurement conditions are considered to be above average. Typical standard ophthalmological conditions would mean a distance of 4 m, dimly lit examination room: 150 lux, UHD LED monitor, 0.1358 pixel pitch.

During the exemplary measurement a conventional personal computer (PC) was used as the computing device 43 and a conventional keyboard 422 as the input device 42. The computing device 43 was in operational connection with the LCD monitor serving as the display 41.

Figure 11:
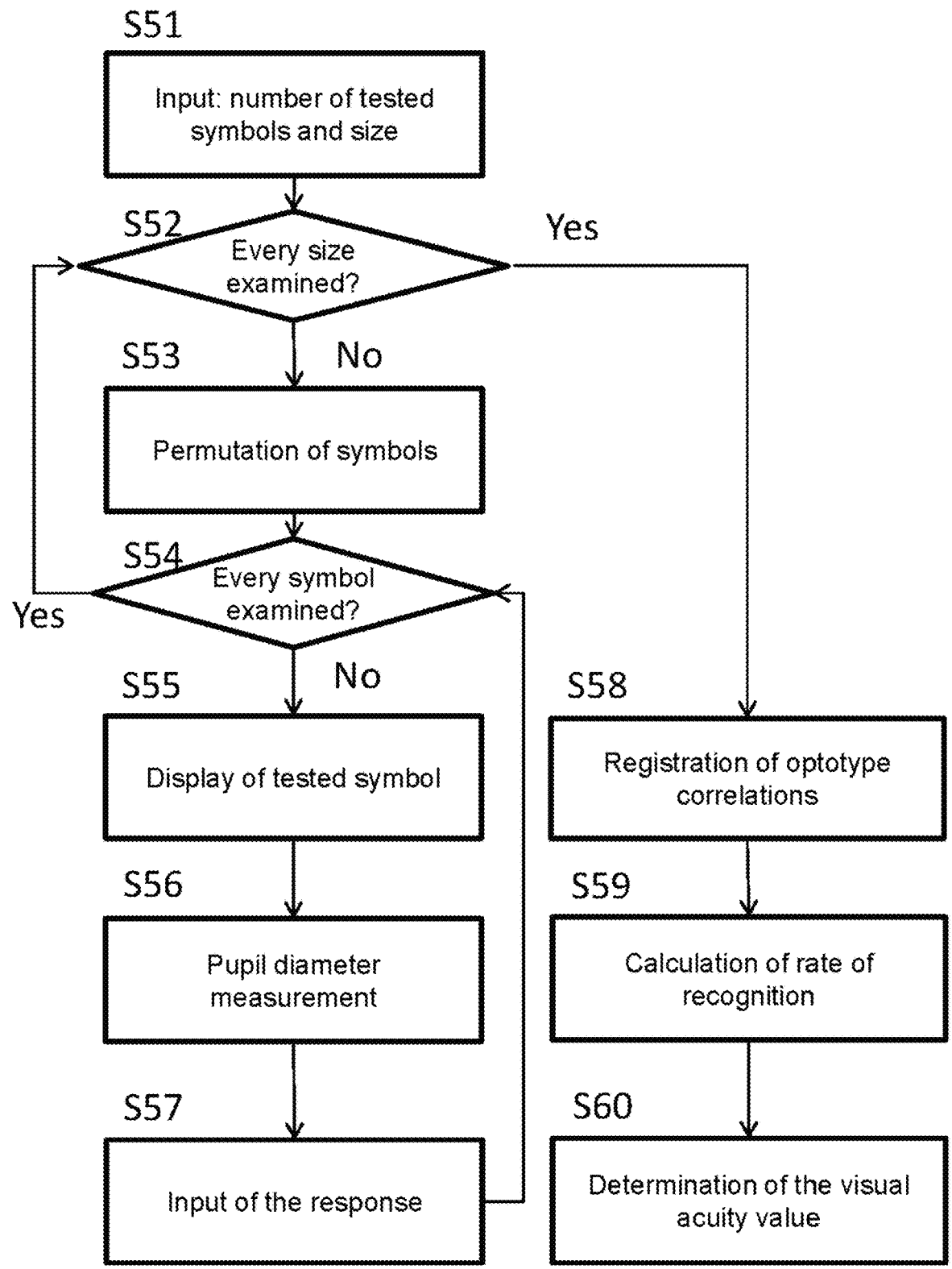
FIG. 11 is a flow chart of a method performed upon execution of a computer program according to the invention.

According to the present example the following measurement was performed upon execution of an exemplary computer program containing computer program instructions stored in the storage medium 432 of the computing device 43. The steps of the measurement are illustrated in FIG. 11.

In Step S51 input parameters were received which input parameters were selected and input through the input device 42 by a user conducting the visual acuity measurement. The user may coincide with the subject whose visual acuity is being measured; however, it is more common to have a separate person conducting the measurement.

The most important input parameters of the program were the optotype sizes (given e.g. as pixel numbers or e.g. as the angle of view) to be displayed and the number of the tested optotypes at a size. The optotype sizes may also be defined by inputting e.g. the largest optotype size and providing an algorithm for choosing the subsequent optotype size to be displayed, which algorithm may choose the next optotype size depending on the subject's ability to recognize the previously displayed optototypes. One of the main advantages of the PC-based setup is that it allows for customized measurements, i.e. the test parameters can be fitted to the currently examined subject. In addition, only one test distance is sufficient to examine subjects in a wide visual acuity range, which ensures easy implementation as well as accurate and reliable results. During the measurement the algorithm of the computer program ran over the optotype sizes (Step S52) and the optotypes (Step S54), and permuted the optotypes in each size (Step S53). In step S52 the algorithm checked whether or not every optotype size has been examined. If not, the algorithm selected the largest optotype size that had not yet been examined, and permuted the optotypes in the selected size in Step S53 resulting in a random sequence of the optotypes at the selected size. This way, the subject could not learn the sequence of the optotypes by heart. In Step S54 the algorithm checked whether or not every optotype had been examined at the selected optotype size. If not, the algorithm caused the computing device 43 to display on the display device 41 (the LCD monitor) in Step S55 one or more optotypes in the obtained sequence at the selected size and wait for a response to be input by the user via the input device 41 in Step S57.

The optotypes were shown on a permanent white background, one by one, whereby crowding had no influence on the measurement. The "one at a time" displaying method further made it possible to examine all the optotypes, in the present case all the twenty six capital letters of the English alphabet in each letter size, instead of the five characters printed in a line on a visual acuity chart according to the prior art. Due to the increased number of tested optotypes this setup provided more information than clinical measurements, which statistically decreased the error of the results. Furthermore, the fact that all the twenty six letters of the English alphabet were examined in each letter size ensured that the subject had to perform exactly the same task for each optotype size, which provided even more reliable acuity scoring. For fourteen letter sizes (covering the normal and supernormal visual acuity range of eye charts, i.e. from 0.3 to $-0.35$ log MAR value) and twenty six optotypes in a row the measurement took approximately half an hour. During the measurements, as in clinical ones, the subject watched the monitor with one eye, while the other was covered with a transparent but opaque shield (i.e. a diffuser) to keep the pupil size at the specific value it was adapted to with both eyes open. In other words, visual acuity is determined separately for the two eyes, hence the two measurements for both eyes of the subject required approximately an hour.

During the present exemplary measurement the response of the subject for every displayed optotype was received in Step S57 before displaying the next optotype at the selected size and the displayed-identified optotype pair was saved for further analysis. For example if the displayed optotype was C but the input response of the subject was D, the saved displayed-identified optotype pair was (C, D).

Since the pupil size significantly influences visual acuity, the pupil diameter was continuously monitored during the visual acuity test with a digital camera in Step S56 e.g. prior to inputting the subject's response in Step S57.

After the subject's response was input the algorithm returned to Step S54 and checked whether or not every optotype (letter) had been examined at the selected optotype size. If not, Steps S55 to S57 were repeated for the following optotype of the optotype sequence obtained in Step S53. If the algorithm determined in Step S54 that every optotype of the selected size had been examined the algorithm returned to Step S52 and checked whether or not every optotype size had been examined. If not, then the largest optotype size was selected that has not yet been examined and Steps S53 to S57 were repeated for the newly selected optotype size.

When the algorithm determined in Step S53 that every optotype size had been examined, in Step S58 the computing device 43 registered a value of similarity for each displayed-identified optotype pair of a given size saved during the previous steps. The value of similarity was calculated as the optotype correlation explained above between the displayed-identified optotype pair, for example where the saved displayed-identified optotype pair was (C, D) the value of similarity registered for the given pair was 0.435 corresponding to row "C" (displayed letter) and column "D" (identified letter) of Table 2. It would have also been possible to register the values of similarity for each displayed-identified optotype pair of a given size directly after receiving the subject's response in Step S57. In this case the values of similarity would have been stored instead or in addition to the displayed-identified optotype pairs.

Once the values of similarity had been registered a rate of recognition was calculated in Step S59 for each optotype size as an average of the registered values of similarity for a given optotype size. For example, for a first optotype size the rate of recognition is calculated as the average of all the values of similarity registered for the displayed-identified optotype pairs where the displayed optotypes were displayed in the first optotype size. It would have also been possible to calculate the rate of recognition for a given optotype size directly after determining in Step S54 that every optotype of the given size had been examined.

Once the rate of recognition for each optotype size had been calculated the visual acuity was determined in Step S60 from the calculated rate of recognition values. This was performed by plotting the rate of recognition values against the reciprocal optotype size v in arc per minutes, fitting a Super Gaussian function SG'(v) on the plotted rate of recognition values, determining the reciprocal letter size $v_0$ for which the Super Gaussian function took the value of 0.68 and regarding this reciprocal letter size $v_0$ as the visual acuity (V) of the subject. The rate of recognition values could have been plotted against the optotype size expressed in log MAR notations and a sigmoid-shape logistic function L'(s) could have been fitted on the plotted values as discussed above in which case the visual acuity (Y) would have been obtained in terms of log MAR.

Although preferred embodiments of the present invention have been illustrated in the accompanying drawings and described in the foregoing detailed description, it is understood that the invention is not limited to embodiments disclosed but is capable of numerous rearrangements, modifications, and substitutions for visual acuity measurements without departing from the invention, as defined by the appended claims.

The invention claimed is:

1. A method for measuring visual acuity of a subject, said method comprising the steps of
    providing a set of optotypes having a pre-calculated value of similarity for each pair of optotypes in the set,
    displaying to the subject sub-sets of optotypes selected from the set of optotypes, each said subset having different optotype size,
    eliciting from the subject, for each displayed optotype a response identifying the displayed optotype,
    registering for each response a value of similarity corresponding to the pre-calculated value of similarity of a pair of optotypes consisting of a displayed optotype and the optotype identified in the response to the displayed optotype,
    calculating a rate of recognition value for each optotype size, the rate of recognition value for a given optotype size being an average of the registered values of similarity for the responses to the optotypes displayed in the given optotype size, and
    determining the visual acuity of the subject from the values of rate of recognition.

2. The method of claim 1, in which the pre-calculated value of similarity is a correlation value calculated for a given pair of optotypes.

3. The method of claim 2, in which the correlation value is optotype correlation, OC, wherein $$OC = \frac{\rho - \bar{\rho}}{1 - \bar{\rho}},$$

ρ is Pearson's correlation value for each pair of optotypes, and $\bar{\rho}$ is an expected value of the Pearson's correlation value distribution without unity values.

4. The method of claim 1, comprising determining the measured visual acuity from the rate of recognition values by
    plotting the rate of recognition values as a function of the corresponding optotype size,
    fitting an interpolation function on the plotted rate of recognition values,
    defining a rate of recognition threshold,
    determining a first optotype size for which the interpolation function takes the value of the rate of recognition threshold,
    calculating the visual acuity from the first optotype size.

5. The method of claim 4, comprising plotting the rate of recognition values against values of reciprocal optotype sizes, wherein each optotype size is expressed as an angle of view of a stroke width of an optotype of the given optotype size; and fitting a Super-Gaussian function as the interpolation function on the rate of recognition values.

6. The method of claim 4, comprising plotting the rate of recognition values against values of optotype sizes, wherein each optotype size (s) is expressed as $$s = \log_{10}(\alpha)$$

wherein α is an angle of view of a stroke width of an optotype of the given optotype size; and fitting a sigmoid-shape logistic function as the interpolation function on the rate of recognition values.

7. The method of claim 1, wherein the optotypes are characters, letters or symbols.

8. A system for measuring visual acuity of a subject, comprising a display device, an input device and a computing device having at least one processor and a storage medium containing a computer program comprising instructions which, when executed by at least one processor of a computing device, it is capable of causing the system to carry out the method according to claim 1.

9. The system of claim 8, in which the computing device is configured to control the display device for generating and displaying images of the optotypes.

10. The system of claim 9, in which the input device comprises a voice recognition module or a tactile reaction recognition module that are operative to receive the responses of the subject.

11. A non-volatile storage medium containing a computer program comprising instructions which, when executed by at least one processor of a computing device operatively connected to a display device and an input device, it is capable of causing the computing device to carry out the method according to claim 1.

* * * * *